US006475993B2

(12) United States Patent
Tremblay

(10) Patent No.: US 6,475,993 B2
(45) Date of Patent: *Nov. 5, 2002

(54) TREATMENT OF HEREDITARY DISEASES WITH GENTAMICIN

(75) Inventor: Jacques P. Tremblay, Bernières (CA)

(73) Assignee: Universite Laval, Quebec (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/469,622

(22) Filed: Dec. 22, 1999

(65) Prior Publication Data

US 2001/0051607 A1 Dec. 13, 2001

(30) Foreign Application Priority Data

Dec. 22, 1998 (CA) .......................................... 2256855

(51) Int. Cl.$^7$ .............................................. A61K 31/70
(52) U.S. Cl. ............................. 514/37; 514/35; 514/36; 514/38; 514/39; 514/40; 514/41
(58) Field of Search .............................. 514/35, 36, 37, 514/38, 39, 40, 41

(56) References Cited

PUBLICATIONS

Anderson, M.D.S. et al., (1992). The molecular and biochemical basis of Duchenne muscular dystrophy. TIBS 17:289–292.
Arahata, K., et al., (1988). Immunostaining of skeletal and cardiac muscle surface membrane with antibody against Duchenne muscular dystrophy peptide. Nature. 333:861–863.
Bedwell, D.M. et al., (1997). Suppression of a CFTR premature stop mutation in a bronchial epithelial cell line. Nature Med. 3:1280–1284.
Bodrug, S.E. et al., (1987). Molecular analysis of a constitutional X–autosome translocation in a female with muscular dystrophy. Science 237: 1620–1624.
Bulman, D. E. et al., (1991). Point mutation in the human dystrophin gene: Identification through Western blot analysis. Genomics 10:457–460.
Chamberlain, J.S. et al., (1991). PCR analysis of dystrophin gene mutation and expression.J. Cell. Biochem. 46:255–259.
Chelly, J. et al., (1990). Effect of dystrophin gene deletions on mRNA levels and processing in Duchenne and Becker muscular dystrophies. Cell. 63: 1239–1248.
Clemens, P.R. et al., (1992). Premature chain termination mutation causing Duchenne muscular dystrophy. Neurology 42:1775–1782.
Hoffman, E.P. et al., (1987). Conservation of the Duchenne muscular dystrophy gene in mice and humans. Science 238:347–350.

Hoffman, E.P. et al., (1987). Dystrophin:The protein product of the Duchenne muscular dystrophy locus. Cell 51: 919–928.
Howard, M. et al., (1996). Aminoglycoside antibiotics restore CFTR function by overcoming premature stop mutations. Nature Med. 2:467–469.
Kilimann, M.W., et al., (1992). Point mutations and polymorphisms in the human dystrophin gene identified in genomic DNA sequences amplified by multiplex PCR. Hum. Genet. 89:253–258.
Koening, M., et al., (1987). Complete cloning of the Duchenne muscular dystrophy (DMD) cDNA and preliminary genomic organization in the DMD gene in normal and affected individuals. Cell 50:509–517.
Menke, A, et al., (1995). Extent of shock–induced membrane leakage in human and mouse myotubes depends on dystrophin. J. Cell Sci. 108:727–733.
Nicholson, L.V.B., et al., (1993). Integrated study of 100 patients with Xp21–linked muscular dystrophy using clinical, genetic, immunochemical and histopathological data. Part 3. Differential diagnosis and prognosis J. Med. Genet. 30:745–751.
Pearce, R.A. et al., (1985). 2,3–Dihydroxybenzoic Acid Arch. Surg. 120:937–940.
Roberts, R. G. (1990). Amplification of illegitimate transcripts. The lancet 336;1523–1526.
Song, B.–B. and J. Schacht (1996). Variable efficacy of radical scavengers and iron chelators to attenuate getamicin ototoxicity in guinea pig in vivo. Hearing Res. 94:87–93.
Sugita, H., et al., (1988). Negative immunostaining of Duchenne muscular dystrophy (DMD) and mdx muscle surface membrane with antibody against synthetic peptide fragment predicted from DMD cDNA. Proc. Japan Acad. 64:37–39.
Corrado, K., et al., (1994). Deletion analysis of dystrophin–actin binding domain. Febs letters 344:255–260.
Hoffman, E.P., et al., (1990). Somatic reversion/suppression of the mouse mdx phenotype in vivo. J. Neurol. Sci. 99:9–25.
Roberts, R.G. et al., (1992). Point mutations in the dystrophin gene. Proc. Natl. Acad. Sci.USA vol. 89. pp. 2331–2335.

*Primary Examiner*—Elli Peselev
(74) *Attorney, Agent, or Firm*—Birch, Stewart, Kolasch & Birch, LLP

(57) ABSTRACT

This invention relates to a method of treating an inherited disease due to a point mutation producing a stop codon by administering an effective dose of an aminoglycoside antibiotic or a derivative thereof. Mdx mouse, which is an animal model for Duchenne muscular dystrophy, has been successfully treated with intramuscularly administered 1 and 5 mg gentamicin, which had for effect to suppress the premature stop mutation by inserting an amino acid at the stop codon. Dystrophin positive muscle fibers not different in number from those of normal mouse were detected at the dose of 5 mg gentamicin.

1 Claim, No Drawings

TREATMENT OF HEREDITARY DISEASES WITH GENTAMICIN

BACKGROUND OF THE INVENTION

Duchenne Muscular Dystrophy (DMD) is due to the mutation of a gene in the X chromosome coding for a protein called dystrophin (Koenig et al 1987; Hoffman et al. 1987; Bodrug et al. 1987, Arahata et al. 1988, Sugita et al. al 1988). The mutations of the dystrophin vary from one family of patients to another but always lead to the absence of a functional dystrophin protein under the membrane on the muscle fiber (Hoffman et al. 1987; Chelly et al. 1990; Chamberlain et al. 1991; Anderson et al 1992; Kilimann et al. 1992; Roberts et al 1992). The absence of dystrophin leads to an increase vulnerability of the muscle fibers during contraction (Menke 1995). Repeated cycles of damages and repairs produce a progressive reduction of the number of muscle fibers and to loss of strength which confine the patients to a wheel chair by the age of ten and to premature death in their early twenties.

Roughly 70% of the mutations of the dystrophin gene are large deletion of one of several exons (Anderson et al 1992; Kilimann et al. 1992). The other mutations are small point mutations due either to a small deletion of a few base pairs leading to a shift of the reading frame or changes of only one base pair producing a missense or a stop codon (Bullman et al 1991. Corrado et al. 1994; Roberts et al. 1992; Clemens et al 1992; Nicholson et al. 1993). Around 5% of all DMD mutations may be due to stop codons.

Cystic fibrosis (CF) is due to a mutation of a gene coding for the CF transmembrane conductance regulator (CFTR) protein. Howard et al. (1996) made experiments with a bronchial epithelial cell line obtained from a CF patient having a premature stop mutation in the CFTR gene. This mutation resulted in a premature end of the synthesis of the CFTR protein and thus in a non-functional protein. They incubated this cell line with aminoglycoside antibiotics G418 (100 mg/mL) or with a gentamicin (200 mg/mL) during 18 to 24 hours. This incubation with gentamicin permitted to suppress the premature stop mutation by inserting an amino acid at the stop codon. A full-length CFTR protein was thus obtained The suppression of the premature stop codon by gentamicin is mediated by mis-pairing between the stop codon and a near-cognate aminoacyl tRNA. Bedwell et al. (1997) recently demonstrated that this full length CFTR protein resulting from the incubation with the aminoglycoside antibiotics was present in the cell membrane and functional.

The mdx mouse is an animal model for DMD. It has a point mutation in the dystrophin gene resulting in a truncated protein which is not incorporated in the muscle fiber membrane (Hoffman et al 1987).

Therefore, this model is proper for testing the effect of aminoglycosides.

SUMMARY OF THE INVENTION

In accordance with the present invention is provided the first method for the in vivo treatment of a disease which is clue to the presence of a premature stop codon in a nucleic acid encoding a protein involved in the etiology of the disease, the method comprising the step of:

administering to the subject an effective dose of an aminoglycoside antibiotic, a derivative thereof or an aminoglycoside-like molecule to suppress the expression of said stop codon.

In a particular embodiment, each mention of the term "aminoglycoside" is intended to mean "gentamicin". Other related molecules or derivatives are within the scope of this invention.

In a preferred embodiment, the aminoglycoside antibiotic is gentamicin sulfate.

The disease that has been treated in practice is Duchenne Muscular Dystrophy. Other diseases caused by a stop mutation would benefit from this invention.

The effective dose of aminoglycoside can be administered intra-muscularly, intravenously or subcutaneously, preferably intramuscularly.

The effective dose is equivalent to about 8 to 40 mg gentamicin sulfate per kg of body weight per day in mice administered intra-muscularly, or to about 1.5 to 6 mg gentamicin sulfate per kg of body weight per day in humans administered intra-muscularly.

Is therefore contemplated a new use of an aminoglycoside antibiotic, a derivative thereof or an aminoglycoside-like molecule in the making of a medication to treat a subject affected by a disease due to the presence of a premature stop codon in a nucleic acid encoding a protein involved in the etiology of the disease, whereby the expression of said stop codon is suppressed and said nucleic acid is correctly translated in to a functional protein.

DESCRIPTION OF THE INVENTION

In the present series of experiments, 4 mdx mice were treated with I.M. injections of gentamicin, two of them received 1 mg/day and the other two 5 mg/day during 7 days. Control normal mice and mdx mice did not receive any gentamicin injections. All mice were then sacrificed, their skeletal muscle and their heart were frozen and cryostat sectioned. The presence of dystrophin in these sections was investigated by immunohistochemistry. Strong dystrophin immunostaining was observed in the normal skeletal and heart muscles. In the untreated mdx muscles, dystrophin immunostaining was observed only in a few revertant fibers (Hoffman et al. 1990). Dystrophin was detected by immunohistochemistry on all muscle fibers and all heart muscle cells of the mdx mice treated with gentamicin. In some muscles of mice treated with 5 mg/day of gentamicin the staining appeared as intense as that observed in the normal mouse muscles. The dystrophin staining was less intense in the muscles of mice treated with 1 mg/kg. This is the first demonstration that an aminoglycoside suppressed in vivo a premature stop codon. Therefore a dose of 8 to 40 mg per Kg of body weight per day successfully suppressed the premature stop codon by inserting an amino acid, and continuing translation of gentamicin-encoding nucleic acids Subcutaneous and intravenous administration would provide the same results. The duration of treatment may vary. For the purpose of the present demonstration, the i.m. treatment lasted for 7 days. Sub-cutaneous or intra-muscular daily treatments of 7 to 14 days or longer have been equivalently successful.

In humans, the usual antibiotic dosage rate of gentamicin is of about 3–5 mg/Kg/day, non-divided dose, for intramuscular route of administration. To avoid toxicity, it is recommended that gentamicin dosage rates be adjusted to avoid blood concentrations higher than 12 $\mu$g/mL for prolonged periods of time. For the purpose of using an optimally effective gentamicin dose, it may be necessary to administer maximal gentamicin doses achieving 12 $\mu$g/mL or higher blood concentration levels In mdx mice, a blood concentration which is about 65 $\mu$g/mL was achieved with a dose of about 35–40 gentamicin mg/Kg/day). No toxicity signs appeared in mdx mice. The blood circulation levels of gentamicin that would be effective in humans have not been calculated, but allometric calculation could bring a dose effective in mice close to an equivalent of about 1.5 to about 6 mg per Kg per day in humans. It is possible to co-administer agents to counteract the oto- or nephrotoxicity of high doses of gentamicin, such as 2,3 dihydroxybenzoate (DHB) as disclosed by Song and Schacht (1996) and by Pearce et al. (1985). Alternatively, aminoglycoside derivatives having an activity towards inserting an amino acid instead of stopping translation may be designed, taking gentamicin as a reference compound. Such gentamicin-like or derived molecules may be more potent than gentamicin and provide fewer toxic side effects. Further, any mean by which gentamicin or gentamicin-like or derived molecules can be driven more directly to the site of action is within the scope of this invention. This would lead to more selective treatment with lower side effects Liposomes or immunoliposomes may be envisageatle, for example, or else, conjugating a gentamicin-related molecule to a ligand specific to muscle tissue (targeting muscle tissue as opposed to systemic dispersion).

Any other disease caused by a stop mutation in nucleic acids of interest, such as certain types of hemophilia, are under the scope of this invention Although the present invention has been described hereinabove by way of a preferred embodiment thereof, this embodiment can be modified at will, within the scope of the appended claims, without departing from the spirit and nature of the subject invention.

REFERENCES

Anderson, M. D. S. and L. M. Kunkel. 1992. The molecular and biochemical basis of Duchenne muscular dystrophy.Elsevier Science Publishers 17; 289–292.

Arahata, K. S. Ishiura, T. Ishiguro, T. Tsukahara, Y. Suhara, C. h. Eguchi, T. Ishihara, I. Nonaka, E. Ozawa and H. Sugita. 1988. Immunostaining of skeletal and cardiac muscle surface membrane with antibody against Duchenne muscle dystrophy peptid.Nature. 333; 851–863.

Bedwell, B. M., KaenjaK. A., Benos. P. J., Bebok, Z., Bubien, J. K., Hong. J., Tousson, A., Clancy, J. P. and Sorscher, E. J. Suppression of a CFTR premature stop mutation in a bronchial epithelial cell line. Nature Med. 3, 1280–1284 (1997).

Bodrug, S. E., P. N. Ray, I. L. Gonzalez, R. D. Schmickel, J. E. Sylvester and R. G. Worton. 1987. Molecular analysis of a constitutional X-autosome translocation in a female with muscular dystrophy.Science 237: 1620–1634.

Bulman, Q. E., S. B. Gangopadhyay, K. G. BebchucK, R. G. Worton and P. N. Ray. 1991. Point mutation in the human dystrophin gene: Identification through Western blot analysis.Genomics 10; 457–460.

Chamberlain, J. S., N. J. Farwell, J. R. Chamberlain, G. A. Cox and C. T. Caskey. 1991. PCR analysis of dystrophin gene mutation and expression.J. Cell. Biochem. 46; 255–259.

Chelly, J. H. Gilgenkrantz, M. Lambert, G. Hamard, P. Chafey, D. Recan, P. Katz, A. De la Chapelle, M. Koenig, I. B. Ginjaar, M. Fardeau, F. Tome, A. Kahn and J. C. Kaplan. 1990. Effect of dystrophin gene deletions on mRNA levels and processing in Duchenne and Becker muscular dystrophies.Cell 63 1239–1248.

Clemens, P. R., P. A. Ward, C. T. Caskey, D. E. Bulman and R. G. Fenwick. 1992. Premature chain termination mutation causing Duchenne muscular dystrophy.Neurology 42: 1775–1782.

Corrado, K., P. L. Mills and J. S. Chamberlain. 1994. Deletion analysis of the dystrophin-actin binding domain. FEBS Letters. 344: 255–260.

Hoffman, E. P., A. P. Monaco, C. C. Feener and L. M. Kunkel. 1987. Conservation of the Duchenne muscular dystrophy gene in mice and humans. Reports. 238: 347–350.

Hoffman, E. P., J. E. Morgan, S. C. Watkins and T. A. Partridge. 1990. Somatic reversion/suppression of the mouse mdx phenotype in vivo.J. Neurol. Sci. 99:9–25.

Hoffman, E. P., L. M. Kunkel and R. H. Brown. Dystrophin: The protein product of the Duchenne muscular dystrophy locus.Cell 51: 919–928 (1987).

Howard, M., Frizzell, R. A. and Bedwell, B. M. Aminoglycoside antibiotics restore CFTR function by overcoming premature stop mutations. Nature Med. 2, 467–469 (1996).

Kilimann, M W., A. Pizzuti, M. Grompe and C. T. Caskey. 1992. Point mutations and polymorphisms in the human dystrophin gene identified in genomic DNA sequences amplified by multiplex PCR.Hum. Genet. 89: 253–258.

Koenig, M., E. P. Hoffman, C. J. Bertelson, A. P. Monaco, C. Feener and L. M. Kunkel. 1987. Complete cloning of the Duchenne muscular dystrophy (PDMD) cDNA and preliminary genomis organization of the DMD gene in normal and affected i.Cell 50: 509–517.

Menke, A. and H. Jockusch. 1995. Extent of shock-induced membrane leakage in human and mouse myotubes depends on dystrophin.J. Cell Sci. 108: 727–733.

Nicholson, L. V. B, M. A. Johnson, K. Bushby, D. Gardner-Medwin. A. Curtis, K. B. GINJAAR, J. T. Den Dunnen. J. L. Welch, T. J. BUTTLER, E. Bakker. G.-J.B. Van Ommen and J. B. Harris. 1993. Integrated study of 100 patients with Xp21-linked muscular dystrophy using clinical, genetic, immunochemical and histopathological data.Journal Med. Genet. 1–25.

Pearce et. al. (1985). Arch. Surg. 120: 937–940.

Roberts, R. G. 1990. Amplification of illegitimate transcripts. The Lancet 336; 1523–1526.

Roberts, R. G., M. Borrow and D. R. Bentley. 1992. Point mutations in the dystrophin gene. Proc. Natl. Acad. Sci USA 89: 2331–2335.

Song and Schacht (1996) Heart Res. 94: 87–93.

Sugita, H., K. Arahata, T. Ishiguro, T. Tsukahara, S Ishiura, C. Eguchi, I. Nonaka, E. Ozawa and Y. Suhara. 1988. Negative immunostaining of Duchenne muscular dystrophy (DMD) and mdx muscle surface membrane with antibody against synthetic peptide fragment predicted from DMD cDNA.Proc. Japan Acad. 64: 37–39.

What is claimed is:

1. A method to treat a subject affected by Duchenne muscular dystrophy disease due to the presence of a premature stop codon in a nucleic acid encoding a protein involved in the etiology of the disease, the method comprising the step of:

administering to the subject an effective dose of a gentamicin antibiotic to suppress the expression of said stop codon.

* * * * *